United States Patent
Park (10) Patent No.: US 12,076,459 B2
(45) Date of Patent: *Sep. 3, 2024

(54) BONE GRAFT COMPOSITION AND MANUFACTURING METHOD THEREOF

(71) Applicant: MedPark Co., Ltd, Busan (KR)

(72) Inventor: JungBok Park, Busan (KR)

(73) Assignee: MedPark Co., Ltd, Busan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/925,337

(22) Filed: Jul. 10, 2020

(65) Prior Publication Data

US 2021/0299325 A1 Sep. 30, 2021

(30) Foreign Application Priority Data

Mar. 31, 2020 (KR) .................. 10-2020-0039211

(51) Int. Cl.
| | | |
|---|---|---|
| A61L 27/20 | (2006.01) | |
| A61L 27/22 | (2006.01) | |
| A61L 27/36 | (2006.01) | |
| A61L 27/56 | (2006.01) | |
| A61L 27/58 | (2006.01) | |

(52) U.S. Cl.
CPC ............ *A61L 27/20* (2013.01); *A61L 27/227* (2013.01); *A61L 27/3608* (2013.01); *A61L 27/56* (2013.01); *A61L 27/58* (2013.01); *A61L 2430/02* (2013.01)

(58) Field of Classification Search
CPC .... A61L 27/20; A61L 27/227; A61L 27/3608; A61L 27/56; A61L 27/58; A61L 2430/02
See application file for complete search history.

(56) References Cited

U.S. PATENT DOCUMENTS

| | | |
|---|---|---|
| 2008/0031917 A1 | 2/2008 | Miller et al. |
| 2012/0205274 A1* | 8/2012 | Sunwoo .............. A61L 27/3608 424/549 |
| 2016/0279287 A1* | 9/2016 | Bachert .............. A61L 24/0036 |
| 2018/0000987 A1 | 1/2018 | Yang et al. |
| 2019/0255216 A1* | 8/2019 | Kalpakci ................. A61L 27/48 |

FOREIGN PATENT DOCUMENTS

| | | |
|---|---|---|
| JP | 04-361757 A | 12/1992 |
| KR | 10-2002-0014034 A | 2/2002 |
| KR | 10-2012-0097521 A | 9/2012 |
| KR | 10-1443814 B1 | 9/2014 |
| KR | 10-2015-0006507 A | 1/2015 |
| KR | 10-2017-0015802 A | 2/2017 |
| KR | 10-1962251 B1 | 5/2017 |
| KR | 101779377 * | 9/2017 |
| KR | 10-2066392 B1 | 5/2019 |

OTHER PUBLICATIONS

Decision to grant a patent mailed Nov. 30, 2020 from Korean Industrial Property Office for Korean Patent Application No. 10-2020-0039211 and its English translation.
Notice of Preliminary Rejection mailed Jun. 24, 2020 from Korean Industrial Property Office for Korean Patent Application No. 10-2020-0039211 and its English translation.

* cited by examiner

*Primary Examiner* — Snigdha Maewall
(74) *Attorney, Agent, or Firm* — Insight Law Group, PLLC; Seung Lee (57) ABSTRACT

The present disclosure relates to a bone graft composition, and more particularly, to a bone graft composition containing hydroxypropyl methylcellulose and a preparation method therefor. Moreover, the present disclosure relates to a bone graft composition that has an optimal composition ratio at which the dissolution rate of hydroxypropyl methylcellulose is excellent.

9 Claims, 3 Drawing Sheets

BONE GRAFT COMPOSITION AND MANUFACTURING METHOD THEREOF

CROSS-REFERENCE TO RELATED APPLICATION (S)

This application claims priority to Korean Patent Application No. 10-2020-0039211, filed on Mar. 31, 2020, the disclosure of which is incorporated herein by reference in its entirety.

BACKGROUND OF THE DISCLOSURE

Technical Field

The present disclosure relates to a bone graft composition having an excellent dissolution rate of hydroxypropyl methylcellulose and a preparation method therefor.

Description of the Related Art

Various materials and various methods may be used for reconstruction of defective bone. For example, bone graft materials such as bone powders, bone chips, and bone blocks may be used, or methods such as autografting, allografting, and xenografting may be used for reconstruction of defective bone.

Bone graft materials that are used for reconstruction of defective bone may be used in orthopedic surgery, neurosurgery, plastic surgery, otolaryngology, Oral and Maxillofacial Surgery, Department of Veterinary Medicine (veterinary clinic), dermatology and dentistry. For example, these materials may be used for bone defects during disc surgery to induce bone regeneration, or may also be used for implant surgery and reconstruction of oral and maxillofacial bone defects.

Meanwhile, Korean Patent No. 10-0401941 discloses technology related to a bone graft material and a preparation method therefor. When a reticular bone is used which is composed of bioceramic powder and has a three-dimensionally communicating pore structure as disclosed therein, there may be limitations in the effect of bone graft in terms of biocompatibility, mechanical properties, toxicity, and the like.

SUMMARY

An object of the present disclosure is to provide a bone graft composition containing hydroxypropyl methylcellulose having a dissolution rate suitable for bone formation, and a preparation method therefor.

One embodiment of the present disclosure provides a bone graft composition containing a bone graft material and hydroxypropyl methylcellulose, wherein the hydroxypropyl methylcellulose reaches a dissolution rate of 50% or more within 48 hours.

One embodiment of the present disclosure provides a bone graft composition wherein the bone graft composition contains the hydroxypropyl methylcellulose in an amount of 0.3 to 3 parts by weight based on 1 part by weight of the bone graft material.

One embodiment of the present disclosure provides a bone graft composition wherein the bone graft material is a natural bone graft material including a porous structure.

One embodiment of the present disclosure provides a method for preparing a bone graft composition, the method including steps of: (1) preparing a bone morphogenetic protein solution by mixing a solvent and a bone morphogenetic protein; (2) adsorbing the bone morphogenetic protein onto graft material powder by mixing the bone morphogenetic protein and the graft material powder; (3) mixing and stirring the graft material powder having the bone morphogenetic protein adsorbed thereon and hydroxypropyl methylcellulose powder to obtain a mixture, and forming a gel from the mixture such that the dissolution rate of the hydroxypropyl methylcellulose powder reaches 50% or more within 48 hours; and (4) forming a structure containing a plurality of pores by freeze-drying the gel under vacuum.

One embodiment of the present disclosure provides a method for preparing a bone graft composition, wherein the bone morphogenetic protein may be at least one selected from the group consisting of BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, recombinant bone morphogenetic proteins thereof, and bone morphogenetic proteins equivalent thereto.

One embodiment of the present disclosure provides a method for preparing a bone graft composition, wherein the concentration of the bone morphogenetic protein in the bone morphogenetic protein solution may be 0.05 to 0.15 mg/ml.

One embodiment of the present disclosure provides a method for preparing a bone graft composition, wherein the pH of the bone morphogenetic protein solution is adjusted to 4.6 to 5 using phosphate buffer saline.

One embodiment of the present disclosure provides a method for preparing a bone graft composition, wherein the volume ratio between the graft material powder having the bone morphogenetic protein adsorbed thereon and the hydroxypropyl methylcellulose powder in step (3) is 1:0.2 to 1:0.8.

One embodiment of the present disclosure provides a method for preparing a bone graft composition, wherein the method further includes a step of sterilizing the bone graft composition by ethylene oxide gas or gamma-ray irradiation.

One embodiment of the present disclosure provides a method for preparing a bone graft composition, wherein the concentration of the ethylene oxide gas is 450 to 1,200 mg/l, or the dose of the gamma-ray irradiation may be 10 to 25 kGy.

DESCRIPTION OF SPECIFIC EMBODIMENTS

Embodiments of the present disclosure relate to a bone graft composition which may have excellent effects in terms of activation of bone formation, biocompatibility, and ease of use by containing a porous bone graft material and hydroxypropyl methylcellulose.

However, description of a portion of a particular embodiment, which overlaps with that of other embodiments, will be omitted for a clearer and more concise explanation. Even though description of that portion is omitted, the portion is not excluded from the present disclosure and the scope of rights thereof should be admitted in the same manner as that of other embodiments.

In the following description, the detailed description of publicly-known technology related to the present disclosure will be omitted when it may unnecessarily obscure the subject matter of the present disclosure. In addition, the terms used in the following description are terms defined in consideration of their functions in the present disclosure and may be changed according to the intention of a user or an operator, or according to practice. Therefore, the definitions of these terms should be determined based on the contents throughout the specification.

The technical spirit of the present disclosure is determined by the claims, and the following embodiments are merely means for efficiently explaining the technical spirit of the present disclosure to those skilled in the art to which the present disclosure pertains.

In the present disclosure, when the repeating unit, compound or resin represented by a formula includes isomers thereof, the corresponding formula representing the repeating unit, compound or resin means a representative formula that also represents the isomers.

Hereinafter, specific embodiments of the present disclosure will be described. However, these embodiments are only examples, and the present disclosure is not limited thereto.

The bone graft composition may be implanted into a bone defect, and may be used to restore the bone defect by filling the bone defect. Hereinafter, 'implant' includes being applied into a bone defect in the state of not having rigidity or in the state of having rigidity. Applying into a bone defect in the state of having rigidity may being implanted into a bone defect after being formed the shape corresponding to the shape of the bone defect in the state of having rigidity by a shape forming device, for example 3 dimensional printer.

A bone graft composition of the present disclosure includes a porous bone graft material and hydroxypropyl methylcellulose. The bone graft composition may be implanted into a bone defect, and may be used to restore the bone defect by filling the bone defect.

The bone graft material may be natural bone, for example, autogenous bone, allogeneic bone, or xenogenic bone. When the natural bone is used, it may exhibit an excellent bone formation effect, because it has excellent biocompatibility and also has good wettability and hygroscopicity due to a large number of pores contained therein. In addition, the natural bone may also be used for reconstruction of defective bone in orthopedic surgery, neurosurgery, plastic surgery, otolaryngology, Oral and Maxillofacial Surgery, Department of Veterinary Medicine (veterinary clinic), dermatology and dentistry.

In addition, the bone graft material may also be used for reconstruction of defective bone in human or animals. Hereinafter, it mainly described the usage to the dentistry, however, the usage does not limited thereto.

As the bone graft composition contains hydroxypropyl methylcellulose, the bone graft composition may have adhesion to a bone defect. In addition, if a predetermined dissolution rate of hydroxypropyl methylcellulose within a predetermined time is satisfied, the function thereof becomes better. When the bone graft composition has excellent adhesion, even if the bone graft composition is applied to the maxilla, it may not flow down, and even if there is an impact due to mastication motion, the bone graft composition may be prevented from being detached from the bone defect.

In order to optimize the solubility of hydroxypropyl methylcellulose, the bone graft composition according to one embodiment of the present disclosure may contain hydroxypropyl methylcellulose in an amount of 0.1 to 6 parts by weight, preferably 0.3 to 3 parts by weight, based on 1 part by weight of the porous bone graft material. In this case, the shape retention ability of the composition is further enhanced.

If the content of the hydroxypropyl methylcellulose is less than 0.3 parts by weight based on 1 part by weight of the porous bone graft material, the hydroxypropyl methylcellulose will dissolve quickly within a short time because the content thereof is low, but a problem may arise in that the hydroxypropyl methylcellulose easily dissolves out because the amount of hydroxypropyl methylcellulose combined with the bone graft material is excessively small, so that the porous bone graft material may not function as a bone graft material. On the other hand, if the content of the hydroxypropyl methylcellulose is more than 3 parts by weight based on 1 part by weight of the porous bone graft material, curing of the hydroxypropyl methylcellulose may occur due to the high content of the hydroxypropyl methylcellulose, and thus the dissolution thereof may be very slow, which may not be suitable for bone formation rate. In addition, in some cases, if the content of the hydroxypropyl methylcellulose is more than 3 parts by weight based on 1 part by weight of the porous bone graft material, a shape in which the hydroxypropyl methylcellulose surrounds the bone graft material can be formed due to an increased volume of the hydroxypropyl methylcellulose, and hence in the humid environment in the oral cavity, the hydroxypropyl methylcellulose can absorb moisture before dissolution thereof occurs, and thus the volume of the bone graft material can increase over time. Accordingly, in order to optimize the solubility of the hydroxypropyl methylcellulose, the content of the hydroxypropyl methylcellulose may be 0.1 to 6 parts by weight, more preferably 0.3 to 3 parts by weight, based on 1 part by weight of the porous bone graft material.

As a solvent for dissolution of the hydroxypropyl methylcellulose, water, for example, may be used. The rate of dissolution formed depending on the dissolution time by hydrating the bone graft composition is expressed as %. For hydration, water is used in an amount of 1 to 1.5 parts by weight, more preferably 1.2 to 1.5 parts by weight, based on 1 part by weight of the bone graft composition that is hydrated. This amount of water is an example of the optimal amount for hydration of the bone graft composition.

A bone graft composition kit according to another embodiment of the present disclosure includes the above-described bone graft composition and a syringe containing the composition. By providing the syringe containing the bone graft composition, it is possible to ensure ease of use and significantly reduce the possibility of contamination that may occur during use.

However, in the description of this embodiment, the description of a portion that overlaps with that of other embodiments is omitted for a clearer and more concise explanation. Even though the description of that portion is omitted, the portion is not excluded from the present disclosure and the scope of rights thereof should be admitted in the same manner as that of other embodiments.

A method for preparing a bone graft composition according to still another aspect of the present disclosure includes steps of: preparing a bone morphogenetic protein solution by adding a bone morphogenetic protein to a solvent or adding the bone morphogenetic protein to the solvent and dissolving the bone morphogenetic protein in the solvent;

mixing and stirring graft material powder having the bone morphogenetic protein adsorbed thereon and hydroxypropyl methylcellulose powder, and forming a viscous gel such that the dissolution rate of the hydroxypropyl methylcellulose powder reaches 50% or more within 48 hours; and forming a sponge-like structure containing a plurality of pores by freeze-drying the mixture of the graft material powder and the hydroxypropyl methylcellulose powder, obtained by the mixing and stirring process, at low temperature under vacuum. The bone graft composition prepared through these steps may have excellent effects in terms of activation of bone formation, biocompatibility, and ease of use.

However, in the description of this embodiment, the description of a portion that overlaps with that of the above-described embodiments is omitted for a clearer and more concise explanation. Even though the description of that portion is omitted, the portion is not excluded from the present disclosure and the scope of rights thereof should be admitted in the same manner as that of the above-described embodiments.

Figure 1:
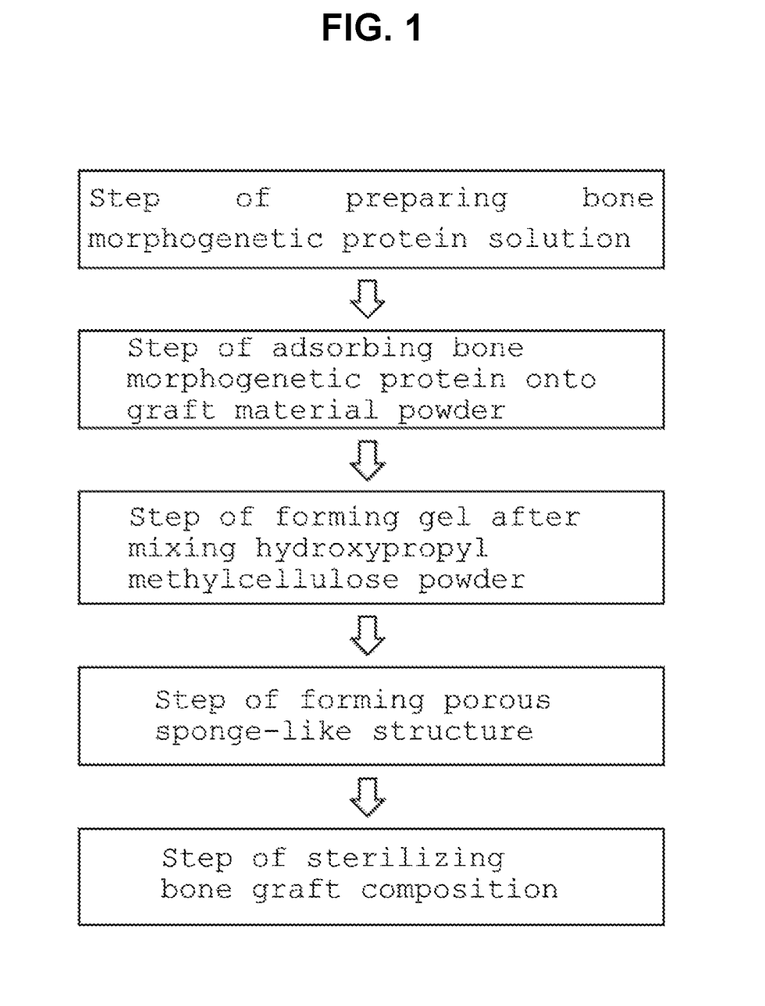
FIG. 1 is a flow diagram schematically showing a method for preparing a bone graft composition according to one embodiment of the present disclosure.

FIG. 1 is a flow diagram schematically showing a method for preparing a bone graft composition according to one embodiment of the present disclosure.

Figure 2:
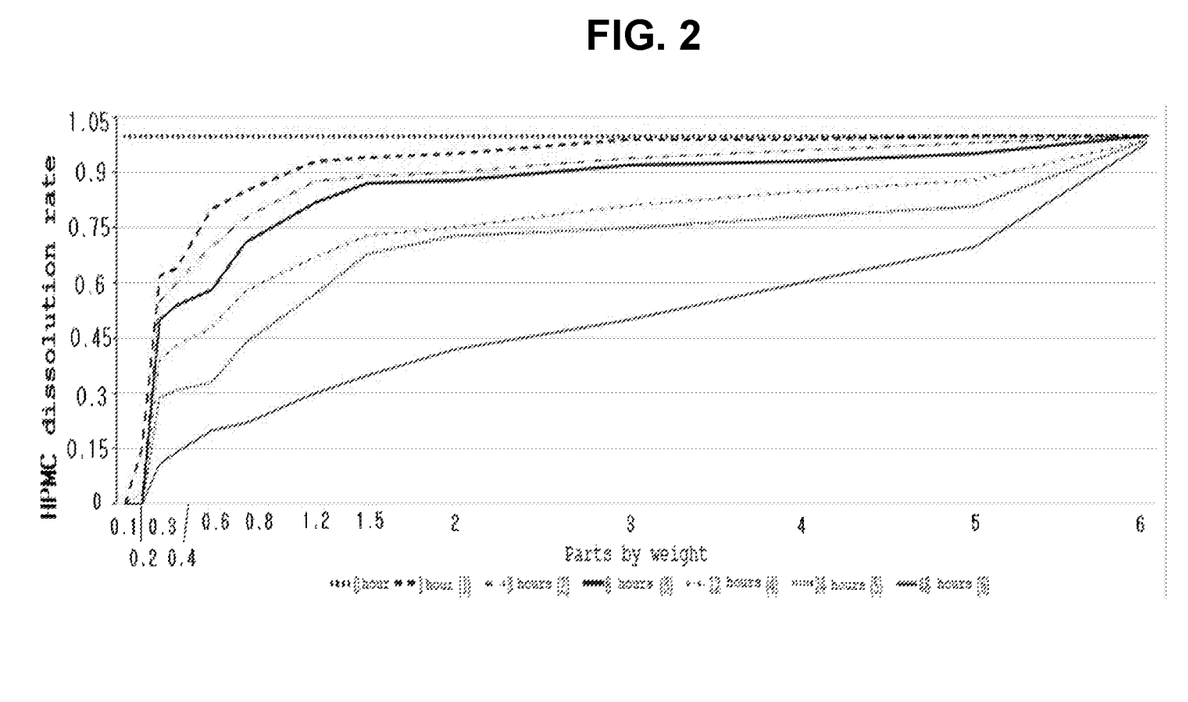
FIG. 2 shows the time-dependent residual rate of hydroxypropyl methylcellulose as a function of the content (parts by weight) thereof, calculated based on the result data (Table 1) obtained in Experimental Example 1 of the present disclosure.

FIG. 2 shows the time-dependent residual rate of hydroxypropyl methylcellulose as a function of the content (parts by weight) thereof, calculated based on the result data (Table 1) obtained in Experimental Example 1 of the present disclosure.

First, a bone morphogenetic protein solution is prepared by dissolving a bone morphogenetic protein in a solvent. The bone morphogenetic protein solution may be prepared by adding the bone morphogenetic protein to the solvent, or adding the bone morphogenetic protein to the solvent and dissolving the bone morphogenetic protein in the solvent.

The bone morphogenetic protein may be at least one selected from the group consisting of BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, recombinant bone morphogenetic proteins thereof, and bone morphogenetic proteins equivalent thereto. Preferably, the bone morphogenetic protein may be rhBMP-2 in terms of the bone formation effect of the present disclosure.

According to one embodiment of the present disclosure, the concentration of the bone morphogenetic protein in the bone morphogenetic protein solution may be 0.05 to 0.15 mg/ml, preferably 0.08 to 0.12 mg/ml. When the concentration of the bone morphogenetic protein is within the above-described range, bone formation by the bone morphogenetic protein may be activated. If the concentration of the bone morphogenetic protein is less than 0.05 mg/ml, the ability of the bone morphogenetic protein to form new bone may be reduced, and if the concentration of the bone morphogenetic protein is more than 0.05 mg/ml, it may cause adverse effects.

In addition, according to one embodiment of the present disclosure, the pH of the bone morphogenetic protein solution may be, for example, 4.6 to 5. When the pH is within the above-described range, bone formation by the bone morphogenetic protein may be activated. If the pH of the bone morphogenetic protein solution is less than 4.6, the ability to form new bone may be reduced, and if the pH of the bone morphogenetic protein solution is more than 5, the ability to form new bone may be reduced. For example, the pH may be adjusted using phosphate buffer saline. When the pH is adjusted using phosphate buffer saline, the bone morphogenetic protein may have the effect of forming new bone.

Thereafter, the bone morphogenetic protein is adsorbed onto graft material powder by soaking the graft material powder with the bone morphogenetic protein solution. The previously prepared graft material powder may be soaked with the bone morphogenetic protein solution by flushing the graft material powder with the bone morphogenetic protein solution or dropping the graft material powder into the bone morphogenetic protein solution, whereby the bone morphogenetic protein may be adsorbed onto the graft material powder.

The graft material powder may be autogenous bone, allogeneic bone, or xenogenic bone. For example, the graft material powder may be prepared by placing it in a snap tube.

The average particle diameter (D50) of the graft material powder may be 200 to 5,000 μm, preferably 250 to 1,000 μm. If the average particle diameter of the powder is less than 200 μm, the graft material may be absorbed rapidly, and thus osteoconduction required for bone formation may be insufficient, and if the average particle diameter of the powder is more than 5,000 μm, precise processing of the graft material powder during application to a patient may be difficult.

According to one embodiment of the present disclosure, the step of adsorbing the bone morphogenetic protein onto the graft material powder may include a step of adsorbing the bone morphogenetic protein using a refrigerated centrifuge.

In some cases, the bone morphogenetic protein may also be suspended in the solution. When the bone morphogenetic protein is adsorbed while it is rotated at high speed using a centrifuge, the bone morphogenetic protein can be prevented from being suspended in the solution, and thus the bone morphogenetic protein may be easily adsorbed onto the surface or into the pores of the graft material powder. Only when the bone morphogenetic protein is adsorbed while it is rotated at high speed, it can be prevented from being suspended again after detachment from the graft material powder. If the bone morphogenetic protein is rotated at low speed, it can be suspended, and hence cannot be easily adsorbed. Under high-speed rotation, the bone morphogenetic protein can be adsorbed quickly onto the surface or into the pores of the graft material powder.

According to one embodiment of the present disclosure, the rotational speed of the refrigerated centrifuge may be 4,000 rpm or more. When the bone morphogenetic protein is adsorbed using the centrifuge, the higher the rotational speed, the better the adsorption. For example, the rotational speed of the centrifuge may be 4,000 rpm or more, and when this rotational speed range is satisfied, the bone morphogenetic protein can be prevented from being suspended in the solution.

According to one embodiment of the present disclosure, the step of adsorbing the bone morphogenetic protein using the refrigerated centrifuge may be performed at a cold temperature of 5° C. or below. As the step of adsorbing the bone morphogenetic protein using the refrigerated centrifuge is performed at a cold temperature of 5° C. or below, it is possible to maximize the effect of adsorbing the bone morphogenetic protein onto the surface or into the pores of the graft material powder through rotation while preventing the denaturation of the bone morphogenetic protein that is weak to heat, by preventing the temperature of the solution from being increased due to rotation. The cold temperature may be a temperature at which the solution does not freeze. For example, the cold temperature may be 5° C. or below, preferably 0.5 to 1.5° C.

Thereafter, the graft material powder having the bone morphogenetic protein adsorbed thereon and hydroxypropyl methylcellulose powder are mixed and stirred to form a gel. The viscous gel thus formed can improve the adhesion of the graft material powder. For example, the stirring may be performed using a mixer. As the graft material powder is stirred with the hydroxypropyl methylcellulose in powder form, a product with homogeneous quality can be obtained.

According to one embodiment of the present disclosure, the volume ratio between the graft material powder having the bone morphogenetic protein adsorbed thereon and the hydroxypropyl methylcellulose powder may be 1:0.2 to 1:0.8. If the volume ratio of the hydroxypropyl methylcellulose powder is less than 0.2, it may be difficult to form a gel, and if the volume ratio of the hydroxypropyl methylcellulose powder is more than 0.8, it may be difficult to form an effective bone graft composition because the volume of the gel is larger than the volume of the graft material powder. In terms of the effects of the disclosure, the volume ratio between the graft material powder having the bone morphogenetic protein adsorbed thereon and the hydroxypropyl methylcellulose powder may preferably be 1:0.6 to 1:0.7.

Thereafter, the mixture of the graft material powder and the hydroxypropyl methylcellulose powder, obtained by the mixing and stirring process, is freeze-dried under vacuum to form a sponge-like structure containing pores. A sponge-like structure containing a plurality of pores may also be formed by freeze-drying the mixture of the graft material powder and the hydroxypropyl methylcellulose powder, obtained by the mixing and stirring process, at a low temperature under vacuum.

A sponge-like structure including a porous structure may be formed by the freeze-drying treatment under vacuum. The gel may be absorbed into the graft material powder to form a sponge-like structure including a porous structure, and it is believed that the treatment under vacuum mainly contributes to the formation of the sponge-like structure including a porous structure.

According to one embodiment of the present disclosure, the method for preparing the bone graft composition may further include a packaging step.

According to one embodiment of the present disclosure, the method for preparing the bone graft composition may further include a step of placing the prepared bone graft composition including a sponge-like structure containing a plurality of pores in a snap tube sized to be inserted into a syringe. When the method further includes the step of placing the composition in a snap tube sized to be inserted into a syringe, the composition may be sized to be inserted into the syringe and thus may be inserted directly into the syringe without a separate process, so that the operation of the process for preparing the bone graft composition can be facilitated.

According to an embodiment of the present disclosure, the method for preparing the bone graft composition may further include a step of placing and sealing the bone graft composition including a sponge-like structure containing a plurality of pores, placed in the snap tube, in a syringe. When the bone graft composition is provided in the syringe, it is possible to ensure ease of use and significantly reduce the possibility of contamination that may occur during use.

According to embodiment of the present one disclosure, the method for preparing the bone graft composition may further include a step of sterilizing the composition.

In one embodiment of the present disclosure, the bone graft composition including a sponge-like structure containing a plurality of pores may be sterilized by ethylene oxide gas. For example, the concentration of the ethylene oxide gas may be 450 to 1,200 mg/l.

If the concentration of the ethylene oxide gas is less than 450 mg/l, sterilization may be insufficient, and if the concentration of the ethylene oxide gas is more than 1,200 mg/l, denaturation of the bone morphogenetic protein may occur.

According to one embodiment of the present disclosure, the bone graft composition including a sponge-like structure containing a plurality of pores may be sterilized by gamma-ray irradiation. For example, the dose of the gamma-ray irradiation may be 10 to 25 kGy. If the dose of the gamma-ray irradiation is less than 10 kGy, sterilization may be insufficient, and if the dose of the gamma-ray irradiation is more than 25 kGy, denaturation of the bone morphogenetic protein may occur.

The bone graft composition prepared according to the above-described method has a certain dissolution rate under certain conditions for application of the composition to the human body, for example, application of the composition to teeth. This dissolution rate may be determined by the content of hydroxypropyl methylcellulose (HPMC) or the like in the bone graft composition.

For example, in the case in which the bone graft composition is applied to teeth, when a dental operator applies the bone graft composition to a missing tooth, the hydroxypropyl methylcellulose (HPMC) contained in the bone graft composition should reach a certain dissolution rate or more within a certain time so that the composition can be applied to the missing tooth with an appropriate adhesion and can fit the shape of the missing tooth. After the bone graft composition is applied to the missing tooth during the medical procedure, the phenomenon that the bone graft composition flows out around or detaches should not occur, and a phenomenon should also not occur in which the hydroxypropyl methylcellulose (HPMC) in the bond graft composition does not dissolve so that the bone graft composition cannot adhere to the bone defect portion, making it impossible to perform the medical procedure. Therefore, the bone graft composition requires critical dissolution conditions of hydroxypropyl methylcellulose (HPMC), and there may occur a difference between the functions thereof depending on the dissolution conditions of hydroxypropyl methylcellulose (HPMC).

When the bone graft composition is applied, the additive hydroxypropyl methylcellulose (HPMC) should reach a dissolution rate of 50% or more within 48 hours so that the composition may effectively function as a bone graft material. If the hydroxypropyl methylcellulose (HPMC) does not reach a dissolution rate of 50% or more within 48 hours, the phenomenon that undissolved hydroxypropyl methylcellulose (HPMC) is cured will occur, and as the curing rate thereof increases, a space in the bone graft composition, into which blood can flow, decreases, so that the composition may not function as a bone graft material.

Meanwhile, if the dissolution rate of the hydroxypropyl methylcellulose (HPMC) reaches 89% or more (a residual rate of less than 11%) within 48 hours, the bone graft composition cannot maintain its shape because the content of the HPMC in the bone graft composition is low. In addition, in this case, the composition cannot aggregate, and hence it is virtually impossible to perform the medical procedure. Furthermore, in this case, even if the medical procedure is completed, the adhesion of the bone graft material may be reduced by physical activities of the person who received the medical procedure, such as salivary gland activity, mastication motion by eating, breathing, conversation, etc., and side effects may occur, such as detachment of the shaped material implanted to fit the defect shape.

Hereinafter, preferred examples will be presented to help the understanding of the present disclosure. However, these examples are merely to illustrate the present disclosure and are not intended to limit the scope of the present disclosure as defined in the appended claims. In addition, it will be obvious to those skilled in the art that various changes and modifications of these examples are possible without departing from the scope and technical spirit of the present disclosure. In addition, it is to be understood that these changes and modifications also fall within the appended claims.

EXPERIMENTAL EXAMPLES

1. Experiment for Examining Residual Amount and Solubility of Hydroxypropyl Methylcellulose (HPMC) Depending on the Content Thereof As shown in Table 1 below, various amounts (0.1 to 6 parts by weight) of HPMC were each added to 0.25 g of a bone graft material. Each of the bone graft material/HPMC mixtures was 10 (water), and the residual amount of the HPMC was examined over time. The amount of HPMC initially added s set to 100% as reference value, and the residual amount of the HPMC remaining after dissolution was expressed as a percentage (%) relative to the reference value (100%). It can be interpreted that the percentage of the residual amount, which is closer to 100%, indicates that little or no dissolution occurred, and the percentage of the residual amount, which is closer to 0%, indicates dissolution of most of the HPMC. In other words, it can be interpreted that when the percentage of the residual amount is 100%, the dissolution rate is 0%, and when the percentage of the residual amount is 0%, the dissolution rate is 100%.

The amount of the solvent (water) corresponds to an optimal degree of hydration to which the mixture can dissolve well. The amount of the solvent is 1 to 1.5 times, for example, 1.2 times, the total weight of the mixture.

TABLE 1

|     | 0 hr | 1 hr | 3 hr | 6 hr | 12 hr | 24 hr | 48 hr |
| --- | --- | --- | --- | --- | --- | --- | --- |
| 0.1 | 100% | 0% | 0% | 0% | 0% | 0% | 0% |
| 0.2 | 100% | 15% | 3% | 0% | 0% | 0% | 0% |
| 0.3 | 100% | 62% | 55% | 50% | 39% | 29% | 11% |
| 0.3 | 100% | 64% | 60% | 54% | 43% | 31% | 14% |
| 0.6 | 100% | 80% | 70% | 58% | 48% | 33% | 20% |
| 0.8 | 100% | 85% | 78% | 71% | 58% | 44% | 22% |
| 1.2 | 100% | 93% | 88% | 82% | 67% | 57% | 30% |
| 1.5 | 100% | 94% | 89% | 87% | 73% | 68% | 35% |
| 2 | 100% | 95% | 90% | 88% | 75% | 73% | 42% |
| 3 | 100% | 99% | 94% | 92% | 81% | 75% | 50% |
| 4 | 100% | 99% | 96% | 93% | 85% | 78% | 60% |
| 5 | 100% | 100% | 98% | 95% | 88% | 81% | 70% |
| 6 | 100% | 100% | 100% | 100% | 99% | 99% | 98% |

As shown in Table 1 above, it can be seen that, as the dissolution time increased, the residual amount decreased and the dissolution rate increased. In addition, it can be seen that, as the amount of hydroxypropyl methylcellulose (HPMC) increased, the residual amount at the same time point increased and the dissolution rate decreased.

FIG. 2 shows the time-dependent residual rate of hydroxypropyl methylcellulose as a function of the content (parts by weight) thereof, calculated based on the result data (Table 1) obtained in Experimental Example 1. In the graph of FIG. 2, a value on the Y-axis, which is closer to 1, indicates a residual rate of 100% (a dissolution rate of 0%), and a value on the Y-axis, which is closer to 0, indicates a residual rate of 0% (a dissolution rate of 100%).

The dissolution of rate the hydroxypropyl methylcellulose in the bone graft composition may require different conditions depending on the application for use of the composition, an environment in which the composition is used, and the purpose of use of the composition. The content ratio between the porous bone graft material and the hydroxypropyl methylcellulose may be determined in consideration of the intended use of the composition and the dissolution time and dissolution rate of the hydroxypropyl methylcellulose.

Under a condition in which 50% or more of hydroxypropyl methylcellulose needs to be dissolved within 48 hours, 0.1 to 3 parts by weight of the hydroxypropyl methylcellulose may be mixed with 1 part by weight of the porous bone graft material to form a bone graft composition. In another example, under a condition in which 60% or more of hydroxypropyl methylcellulose needs to be dissolved within 48 hours, 0.1 to 2 parts by weight of the hydroxypropyl methylcellulose may be mixed with 1 part by weight of the porous bone graft material to form a bone graft composition. In still another example, under a condition in which 70% or more of hydroxypropyl methylcellulose needs to be dissolved within 48 hours, 0.1 to 1.2 parts by weight of the hydroxypropyl methylcellulose may be mixed with 1 part by weight of the porous bone graft material to form a bone graft composition. In yet another example, under a condition in which 80% or more of hydroxypropyl methylcellulose needs to be dissolved within 48 hours, 0.1 to 0.6 parts by weight of the hydroxypropyl methylcellulose may be mixed with 1 part by weight of the porous bone graft material to form a bone graft composition. In consideration of the functional aspect of the bone graft material, 0.3 parts by weight or more of the hydroxypropyl methylcellulose is preferably mixed with 1 part by weight of the porous bone graft material.

In another example, under a condition in which 50% or more of hydroxypropyl methylcellulose needs to be dissolved within 24 hours, 0.1 to 1.0 part by weight of the hydroxypropyl methylcellulose may be mixed with 1 part by weight of the porous bone graft material to form a bone graft composition. In addition, in consideration of the functional aspect of the bone graft material, 0.3 to 1.0 part by weight of the hydroxypropyl methylcellulose may be mixed with 1 part by weight of the porous bone graft material to form a bone graft composition.

In another example, under a condition in which 50% or more of hydroxypropyl methylcellulose needs to be dissolved within 12 hours, 0.1 to 0.6 parts by weight of the hydroxypropyl methylcellulose may be mixed with 1 part by weight of the porous bone graft material to form a bone graft composition. In addition, in consideration of the functional aspect of the bone graft material, 0.3 to 0.6 parts by weight of the hydroxypropyl methylcellulose may be mixed with 1 part by weight of the porous bone graft material to form a bone graft composition.

Experimental Example 2

2. Experiment for Examining Volume Reduction Rate and Solubility Depending on Content of Hydroxypropyl Methylcellulose (HPMC)

As shown in Table 2 below, various amounts (0.1 to 6 parts by weight) of HPMC were each added to 0.25 g of a bone graft material. Each of the bone graft material/HPMC mixtures was dissolved (hydrated) in a solvent (water), and the residual amount of the HPMC was examined over time. Specifically, the hydrated sample is placed closely in a 15-ml conical tube, and then the initial volume thereof was measured, and then the portion not occupied by the sample was cut from the conical tube. Next, the opening of the conical tube remaining after cutting was covered with a mesh so that only the dissolved portion of the sample could through the opening.

Thereafter, the conical tube was placed in an ultrasonic cleaner maintained at the human body temperature (for example, 37° C.), and purified water was circulated at a constant flow rate, and after 48 hours, the volume of the sample was measured. Before measurement of the volume of the sample, purified water remaining in the sample may be removed.

Depending on the amount of HMPC added, the volume reduction rate in the environment similar to that in the human body was measured. It can be interpreted that a higher volume reduction rate indicates a higher dissolution rate of the sample, and a lower volume reduction rate indicates a lower solubility of the sample.

The amount of the solvent (water) corresponds to an optimal degree of hydration to which the mixture can dissolve well. The amount of the solvent is 1 to 1.5 times, for example, 1.2 times, the total weight of the mixture.

TABLE 2

| Parts by weight of HPMC | Initial volume (cc) | Volume (cc) after 48 hours | Volume reduction rate (%) |
| --- | --- | --- | --- |
| 0.1 | 0.270 | 0.101 | 62.58% |
| 0.2 | 0.529 | 0.307 | 42.01% |
| 0.3 | 0.652 | 0.544 | 16.54% |
| 0.4 | 0.766 | 0.683 | 10.82% |
| 0.6 | 1.131 | 1.010 | 10.70% |
| 0.8 | 1.275 | 1.136 | 10.92% |
| 1.2 | 1.987 | 1.791 | 9.85% |
| 1.5 | 2.312 | 2.090 | 9.61% |
| 2 | 2.768 | 2.544 | 7.73% |
| 3 | 4.080 | 3.816 | 6.46% |
| 4 | 4.378 | 4.728 | −7.99% |
| 5 | 5.426 | 5.954 | −9.72% |
| 6 | 5.672 | 6.322 | −1.46% |

TABLE 3

| Parts by weight of HPMC | Initial weight (g) | Weight (g) after 48 hours |
| --- | --- | --- |
| 0.1 | 1.630 | 0.610 |
| 0.2 | 3.190 | 1.850 |
| 0.3 | 3.930 | 3.280 |
| 0.4 | 4.620 | 4.120 |
| 0.6 | 6.820 | 6.090 |
| 0.8 | 7.690 | 6.850 |
| 1.2 | 11.980 | 10.800 |
| 1.5 | 13.940 | 12.600 |
| 2 | 16.690 | 15.400 |
| 3 | 24.600 | 23.010 |
| 4 | 26.400 | 28.510 |
| 5 | 32.720 | 35.900 |
| 6 | 34.200 | 38.120 |

As shown in Tables 2 and 3 above, it can be seen that, depending on the content (parts by weight) of HPMC, the volume and weight of the sample changed after 48 hours in the human body environment. In addition, it can be seen that, as the content of hydroxypropyl methylcellulose (HPMC), the residual amount of the HPMC increased and the dissolution rate thereof decreased.

Figure 3:
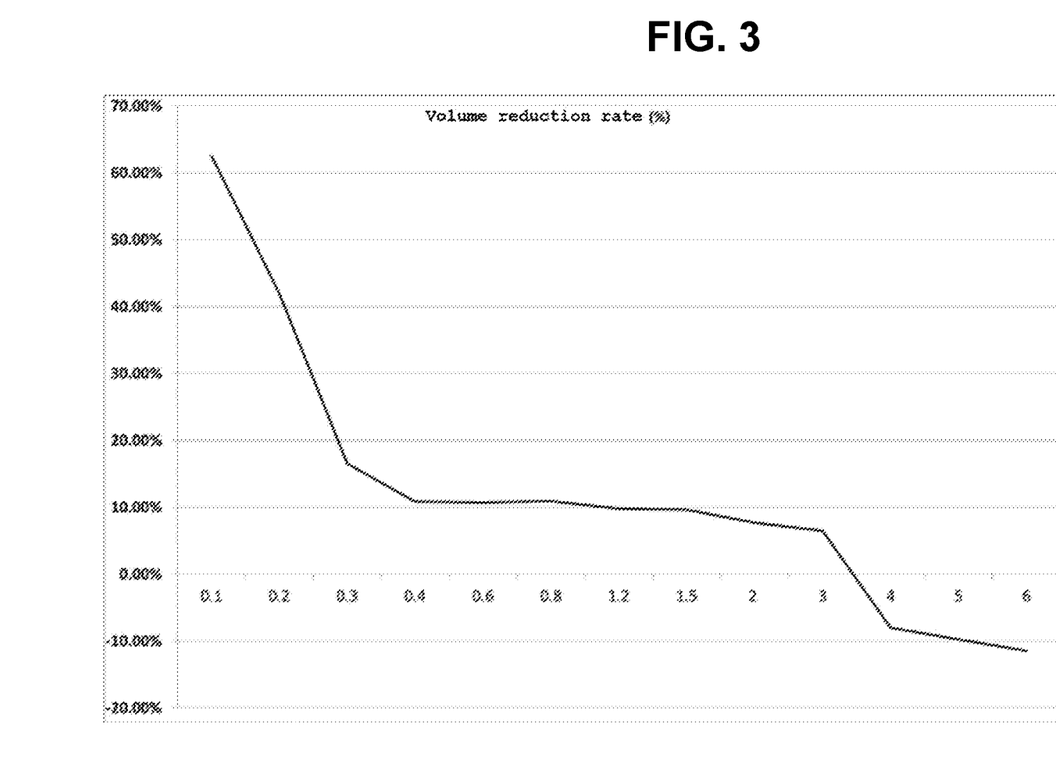
FIG. 3 shows volume reduction rates depending on the content (parts by weight) of hydroxypropyl methylcellulose, calculated based on the result data (Table 2) obtained in Experimental Example 2 of the present disclosure.

FIG. 3 shows volume reduction rates depending on the content (parts by weight) of hydroxypropyl methylcellulose (HPLC), calculated based on the result data (Table 2) obtained in Experimental Example 2 of the present disclosure.

As shown in FIG. 3, it can be seen that, when the content of the HPMC in the bone graft composition was 0.2 parts by weight, the volume reduction rate was 40%, and when the content of the HPMC was 0.3 parts by weight, the volume reduction rate decreased rapidly to 16.54%. In addition, it can be seen that, when the content of the HPMC was 0.2 parts by weight, the volume reduction rate was 40%, and when the content of the HPMC in the bone graft composition was 3 parts by weight, the volume reduction rate was decreased rapidly to 6.46%, but when the content of the HPMC was 4 parts by weight, the volume reduction rate has a negative value.

This means that, when the content of the HPMC is less than 0.3 parts by weight based on 1 part by weight of the bone graft material, the HPMC dissolves too quickly and flows out in the human body environment and flows out, and hence the volume of the sample is not maintained and the HPMC can neither promote nor help bone formation. On the other hand, if the content of the HPMC is more than 3 parts by weight based on 1 part by weight of the bone graft material, the volume of the HPMC becomes greater than the volume of the bone graft material, and thus a phenomenon will arise in which a shape in which the HPMC surrounds the bone graft material is formed, and thus the volume becomes larger while the HPMC absorbs external moisture.

As can be seen in Table 3 above, this can be confirmed from the fact that when the content of the HPMC was more than 3 parts by weight based on 1 part by weight of the bone graft material, the weight of the sample after the experiment rather increased due to absorption of external moisture.

Accordingly, in order to achieve the functional aspect of the bone graft material, 0.3 to 3 parts by weight may be mixed with 1 part by weight of the porous bone graft material.

As described above, the bone graft composition containing hydroxypropyl methylcellulose according to the present disclosure has an excellent dissolution rate of hydroxypropyl methylcellulose within a certain time, and thus has excellent effects in terms of activation of bone formation, biocompatibility, and ease of use.

What is claimed is:

1. A bone graft composition comprising:
   a bone graft material; and
   hydroxypropyl methylcellulose, wherein the hydroxypropyl methylcellulose combined with the bone graft composition reaches a dissolution rate of 50% or more within 48 hours to secure for a space in the bone graft composition, into which blood can flow, wherein the hydroxypropyl methylcellulose combined with the bone graft composition reaches the dissolution rate of less than 89% within 48 hours to maintain the shape within the bone defect portion and to be aggregated during a medical procedure, wherein the bone graft composition comprises the hydroxypropyl methylcellulose in an amount of 0.3 to 3 parts by weight based on 1 part by weight of the bone graft material, and wherein the dissolution rate of 50% or more and less than 89% is obtained in an amount of 1.2 to 1.5 parts by weight of a solvent based on 1 part by weight of the bone graft composition, wherein the bone graft material is a natural bone graft material comprising a porous structure, and wherein the bone graft composition is generated from a mixture having a volume ratio of graft material powder having bone morphogenetic protein adsorbed thereon with respect to the hydroxypropyl methylcellulose of 1:0.2 to 1:0.8.

2. The bone graft composition of claim 1, wherein the dissolution rate of 50% or more and less than 89% is obtained in an amount of 1.2 parts by weight of a solvent based on 1 part by weight of the bone graft composition.

3. The bone graft composition of claim 1, wherein the solvent is water.

4. A bone graft composition consisting of:
a bone graft material; and
hydroxypropyl methylcellulose,
wherein the hydroxypropyl methylcellulose combined with the bone graft composition reaches a dissolution rate of 50% or more within 48 hours to secure for a space in the bone graft composition, into which blood can flow, wherein the hydroxypropyl methylcellulose combined with the bone graft composition reaches the dissolution rate of less than 89% within 48 hours to maintain the shape within the bone defect portion and to be aggregated during a medical procedure, wherein the dissolution rate of 50% or more and less than 89% is obtained in an amount of 1 to 1.5 parts by weight of a solvent based on 1 part by weight of the bone graft composition, wherein the bone graft material is a natural bone graft material comprising a porous structure, and wherein the bone graft composition is generated from a mixture having a volume ratio of graft material powder having bone morphogenetic protein adsorbed thereon with respect to the hydroxypropyl methylcellulose of 1:0.2 to 1:0.8.

5. The bone graft composition of claim 4, wherein the hydroxypropyl methylcellulose is in an amount of 0.3 to 3 parts by weight based on 1 part by weight of the bone graft material.

6. The bond graft composition of claim 5, wherein the dissolution rate of 50% or more and less than 89% is obtained in an amount of 1.2 to 1.5 parts by weight of a solvent based on 1 part by weight of the bone graft composition.

7. The bone graft composition of claim 5, wherein the dissolution rate of 50% or more and less than 89% is obtained in an amount of 1.2 parts by weight of a solvent based on 1 part by weight of the bone graft composition.

8. The bone graft composition of claim 5, wherein the solvent is water.

9. The bone graft composition of claim 1, wherein the bone graft composition is generated from a mixture having a volume ratio of the graft material powder having the bone morphogenetic protein adsorbed thereon with respect to the hydroxypropyl methylcellulose of 1:0.6 to 1:0.7.

* * * * *